(12) United States Patent
Birnbaum et al.

(10) Patent No.: US 8,224,418 B2
(45) Date of Patent: Jul. 17, 2012

(54) INTEGRAL HEART RATE MONITORING GARMENT

(75) Inventors: Burton H. Birnbaum, Lake Worth, FL (US); Mika Petri Sorvisto, Kempele (FI)

(73) Assignee: Polar Electro Oy, Kempele (FI)

( * ) Notice: Subject to any disclaimer, the term of this patent is extended or adjusted under 35 U.S.C. 154(b) by 836 days.

(21) Appl. No.: 11/019,681

(22) Filed: Dec. 21, 2004

(65) Prior Publication Data
US 2006/0135863 A1 Jun. 22, 2006

(51) Int. Cl.
*A61B 5/04* (2006.01)
*A61M 5/32* (2006.01)
*A61F 13/15* (2006.01)
*A61F 13/00* (2006.01)

(52) U.S. Cl. ........ 600/388; 600/380; 600/509; 604/179; 604/386; 128/889

(58) Field of Classification Search .................. 600/388, 600/390, 509; 604/179, 396; 128/889
See application file for complete search history.

(56) References Cited

U.S. PATENT DOCUMENTS

| | | | |
|---|---|---|---|
| 4,041,394 A * | 8/1977 | Pate .............................. | 455/100 |
| 4,055,166 A | 10/1977 | Simpson et al. | |
| 4,367,752 A | 1/1983 | Jimenez et al. | |
| 4,875,238 A * | 10/1989 | Solomon et al. ................. | 2/115 |
| 4,889,131 A * | 12/1989 | Salem et al. ................. | 600/484 |
| 5,078,134 A | 1/1992 | Heilman et al. | |
| 5,353,793 A | 10/1994 | Bornn | |
| 5,464,021 A * | 11/1995 | Birnbaum ..................... | 600/509 |
| 5,944,669 A | 8/1999 | Kaib | |
| 6,032,289 A | 3/2000 | Villapiano | |
| 6,205,346 B1 | 3/2001 | Akiva | |
| 6,419,636 B1 | 7/2002 | Young et al. | |
| 6,551,252 B2 * | 4/2003 | Sackner et al. .............. | 600/536 |
| 6,589,171 B2 | 7/2003 | Keirsbilck | |
| 6,687,523 B1 * | 2/2004 | Jayaramen et al. ........... | 600/388 |
| 6,714,812 B1 | 3/2004 | Karjalainen et al. | |
| 6,727,197 B1 * | 4/2004 | Wilson et al. ................. | 442/301 |
| 6,736,759 B1 | 5/2004 | Stubbs et al. | |

(Continued)

FOREIGN PATENT DOCUMENTS

WO WO 01/67723 A1 9/2001
(Continued)

OTHER PUBLICATIONS

Website content—http://www.polarusa.com/store/productdetail.asp?ProdID=4—Heart Bra Product ID: 3100514, Sep. 29, 2004.

*Primary Examiner* — Nicole F Lavert
(74) *Attorney, Agent, or Firm* — Hoffmann & Baron, LLP

(57) ABSTRACT

A garment adapted for monitoring a user's heart rate includes material, a transmitter, one or more electrodes, and a power source. The transmitter, electrodes, and power source are integrated with the material. The electrodes and power source are operatively coupled to the transmitter, and the electrodes are responsive to the user's heart rate. The garment is adapted for being worn, washed, and discarded with the electrodes, transmitter, and power source integrated therewith. A method of monitoring heart rate includes integrating a transmitter, electrodes, and power source with a garment, coupling the electrodes operatively to the transmitter, coupling the power source operatively to the transmitter, and adapting the garment for being worn, washed, and discarded with the transmitter, electrodes, and power source integrated therewith.

21 Claims, 8 Drawing Sheets

U.S. PATENT DOCUMENTS

| | | |
|---|---|---|
| 6,774,800 B2 | 8/2004 | Friedman et al. |
| 2003/0045787 A1 | 3/2003 | Schulze et al. |
| 2003/0050539 A1 | 3/2003 | Naghavi et al. |
| 2003/0184575 A1 | 10/2003 | Reho et al. |
| 2003/0212319 A1* | 11/2003 | Magill .................. 600/382 |
| 2004/0009731 A1 | 1/2004 | Rabinowicz |
| 2004/0027246 A1* | 2/2004 | Aguglia ................ 340/573.1 |
| 2004/0059387 A1 | 3/2004 | Yu |
| 2004/0078219 A1 | 4/2004 | Kaylor et al. |
| 2004/0100376 A1 | 5/2004 | Lye et al. |
| 2004/0138546 A1 | 7/2004 | Reho et al. |
| 2004/0210980 A1* | 10/2004 | Cacioli et al. ............ 2/159 |
| 2005/0054941 A1* | 3/2005 | Ting et al. ............. 600/529 |

FOREIGN PATENT DOCUMENTS

| | | |
|---|---|---|
| WO | WO 02/059923 | 8/2002 |
| WO | WO 03/075693 | 9/2003 |

* cited by examiner

INTEGRAL HEART RATE MONITORING GARMENT

BACKGROUND OF THE INVENTION

1. Field of the Invention

The present invention relates generally to heart rate monitors, and more particularly relates to a heart rate monitoring garment adapted for being worn, washed, and discarded with an integral transmitter, power source, and electrodes.

2. Description of the Related Art

Personal heart rate measurement devices or monitors noninvasively measure a user's heart rate and are commonly used by sports enthusiasts and athletes. As shown in FIG. 1, the heart rate monitor preferably includes a transmitter unit 10, which includes one or more electrodes 12 and a transmitter 14 attached to a belt 16 worn around the user's chest. The heart rate monitor also includes a receiver unit 18, which includes a microprocessor, user interface, and display 20 attached to a wristband 22. The transmitter unit 10 is in telemetric, inductive, and/or optical connection with the receiver unit 18.

The user's heart rate is preferably measured by the heart rate monitor in terms of the number of heartbeats that occur during a unit of time, such as beats per minute. The electrodes 12 detect electrical signals generated by the heart, and the display 20 shows the measured heart rate to the user. The display 18 can show additional information, such as predetermined heart rate limits or target zones.

However, users are likely to find that the band 16 of the transmitter unit 10 is overly restrictive, obtrusive, and often slips during use since the band 16 has limited contact with the body and needs to be tight to remain in the correct position. The band 16 also requires a high degree of elasticity and the materials most conducive to this feature, such as plastic or rubber, typically trap moisture from perspiration, which causes conventional heart rate monitors to be uncomfortable when used on a regular basis.

Further, the conventional band 16 requires the additional steps of strapping it on, adjusting it to the user's chest dimensions, and at least periodic cleaning. The band 16 also represents another piece of equipment, in addition to athletic shoes, towels, socks, shirt, shorts, and audio equipment, which are typically used during an exercise session.

OBJECTS AND SUMMARY OF THE INVENTION

It is an object of the present invention to provide an effective and reliable method and apparatus that integrate a transmitter, power source, and electrodes of a heart rate monitor with a wearable garment.

It is a further object of the present invention to provide a garment having an embedded heart rate transmitter, power source, and electrodes that can be worn, washed, and discarded as an integral unit.

It is still a further object of the present invention to provide a method and apparatus for reducing the quantity of equipment required during exercise or athletic activities.

It is another object of the present invention to provide a method and apparatus for making a heart rate monitor less restrictive, obtrusive, or likely to slip and more comfortable to wear.

These and other goals and objectives of the present invention provide a garment adapted for monitoring a user's heart rate. The garment includes material, a transmitter, one or more electrodes, and a power source. The transmitter, electrodes, and power source are integrated with the material. The electrode and power source are operatively coupled to the transmitter, and the electrode is responsive to the user's heart rate. The transmitter is adapted for providing information, such as a signal, representative of the user's heart rate. The garment is adapted for being worn, washed, and disposable with the electrode, transmitter, and power source integrated therewith.

The present invention also provides a method of monitoring heart rate including integrating a transmitter, electrode, and power source with a garment, and coupling the electrode operatively to the transmitter. The method also includes coupling the power source operatively to the transmitter, and adapting the garment for being worn, washed, and disposable with the transmitter, electrode, and power source integrated therewith.

These and other objects, features, and advantages of this invention will become apparent from the following detailed description of illustrative embodiments thereof, which is to be read in connection with the accompanying drawings.

DETAILED DESCRIPTION OF THE PREFERRED EMBODIMENTS

Figure 2:
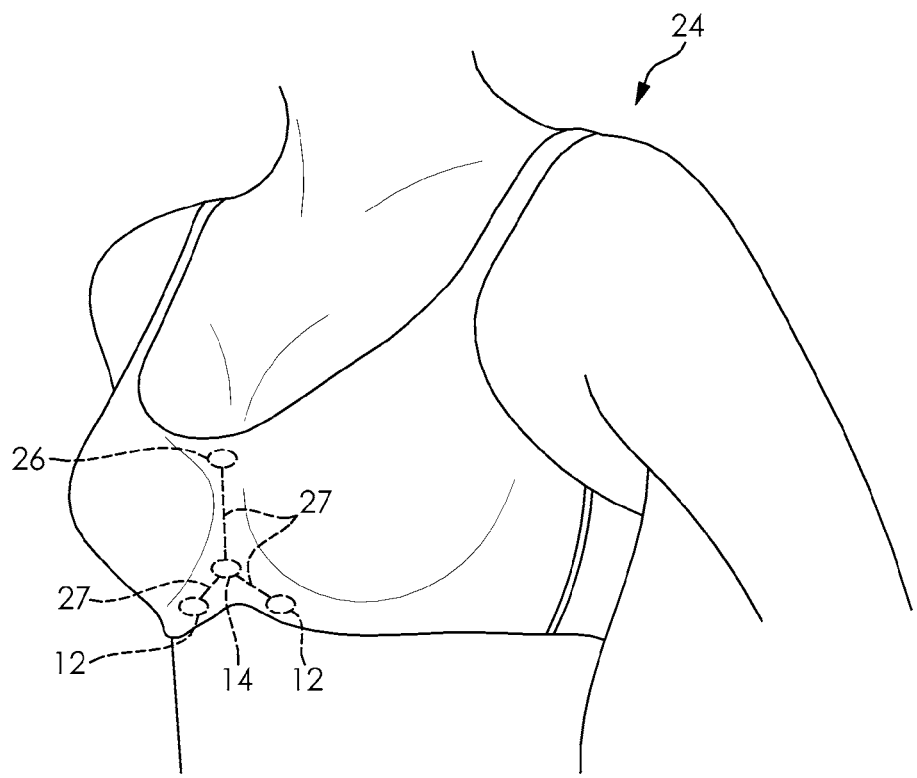
FIG. 2 is a pictorial diagram of a brassiere incorporating an integral transmitter, power source, and electrodes formed in accordance with the present invention.

FIG. 2 shows a pictorial diagram of a heart rate monitoring garment 24 formed in accordance with the present invention. The garment 24 incorporates a transmitter 14, one or more electrodes 12, and a power source 26 embedded in or integrated with the garment 24, which are preferably adapted to be inseparable from the garment 24 without fracturing the garment 24, such as by removing stitching or welding. The garment 24 is shown in FIG. 2 in the form of a brassiere, but can assume a variety of different forms while remaining within the scope of the present invention.

The electrodes 12 and power source 26 are preferably coupled electrically to the transmitter 14, as indicated by dashed lines 27 connecting these elements. The electrical connections between the transmitter 14, electrodes, and power source 26 are preferably not visible to the user. Any or all of the transmitter 14, electrodes 12, and power source 26 may be collocated, collinearly located, and/or placed at different positions throughout the garment 24 while remaining within the scope of the present invention.

Figure 1:
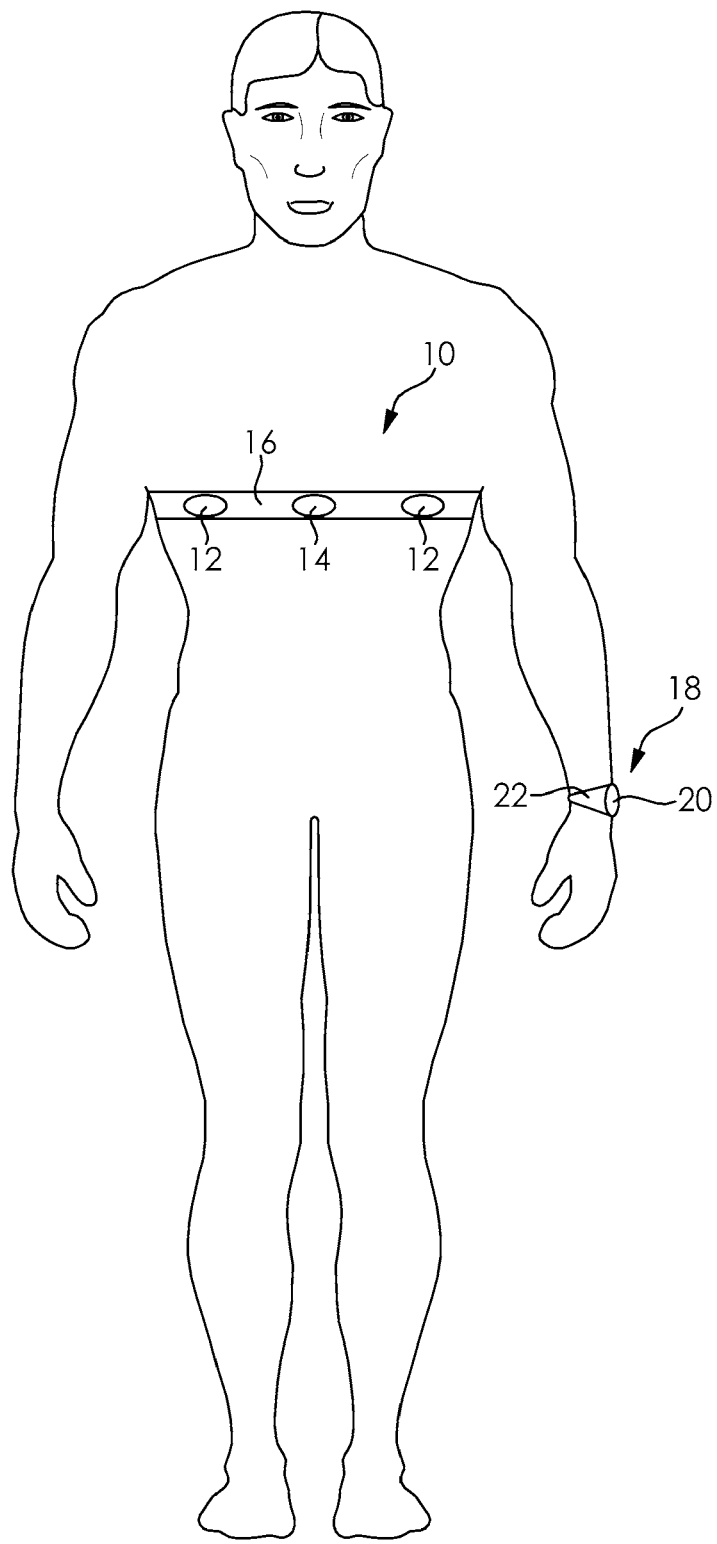
FIG. 1 is a pictorial diagram of a conventional heart rate monitor including a transmitter unit and receiver unit.

The electrodes 12 preferably detect electrocardiograph signals, when positioned about the user's chest. Alternatively, the electrodes 12 preferably take the form of optical sensors or pressure sensors if heart rate measurements are obtained from locations other than the chest, such as the wrist, finger, or ankle. Signals from the electrodes 12 are provided to the transmitter 14, which provides information obtained from the signals to a receiver unit (not shown in FIG. 2), such as that shown in FIG. 1, by wired or wireless means for further processing, analysis, and/or display to the user. The transmitter 14 may also or alternatively store information obtained from the signals in, for instance, memory, which may relieve the necessity of using the receiver unit with the heart rate monitor. The stored information may then be downloaded to, for instance, a personal computer for further processing, analysis, and/or display.

Figure 3:
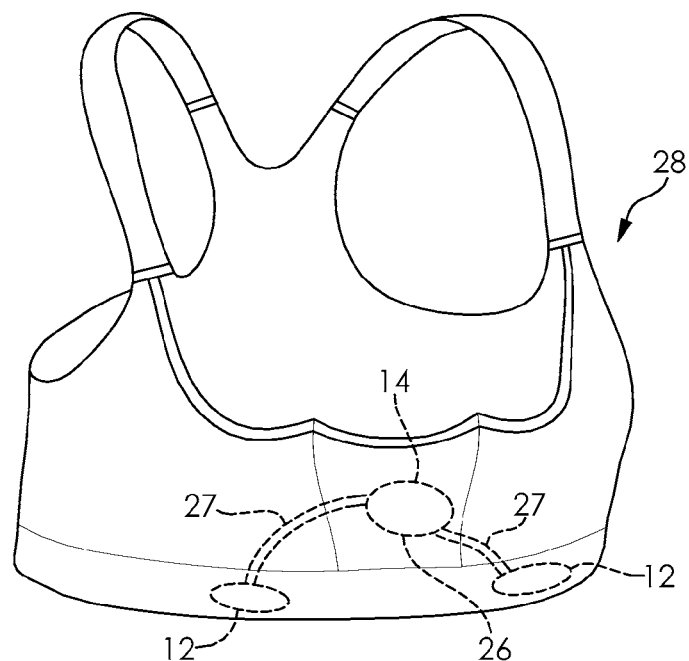
FIG. 3 is a pictorial diagram of a sports brassiere in accordance with the present invention.

FIG. 3 shows a pictorial diagram of a second embodiment of the heart rate monitoring garment 28, in which the electrodes 12, transmitter 14, and power source 26 are integrated with the garment 28 in the form of a sports brassiere. In this embodiment, the power source 26 has been collocated with the transmitter 14.

Figure 4:
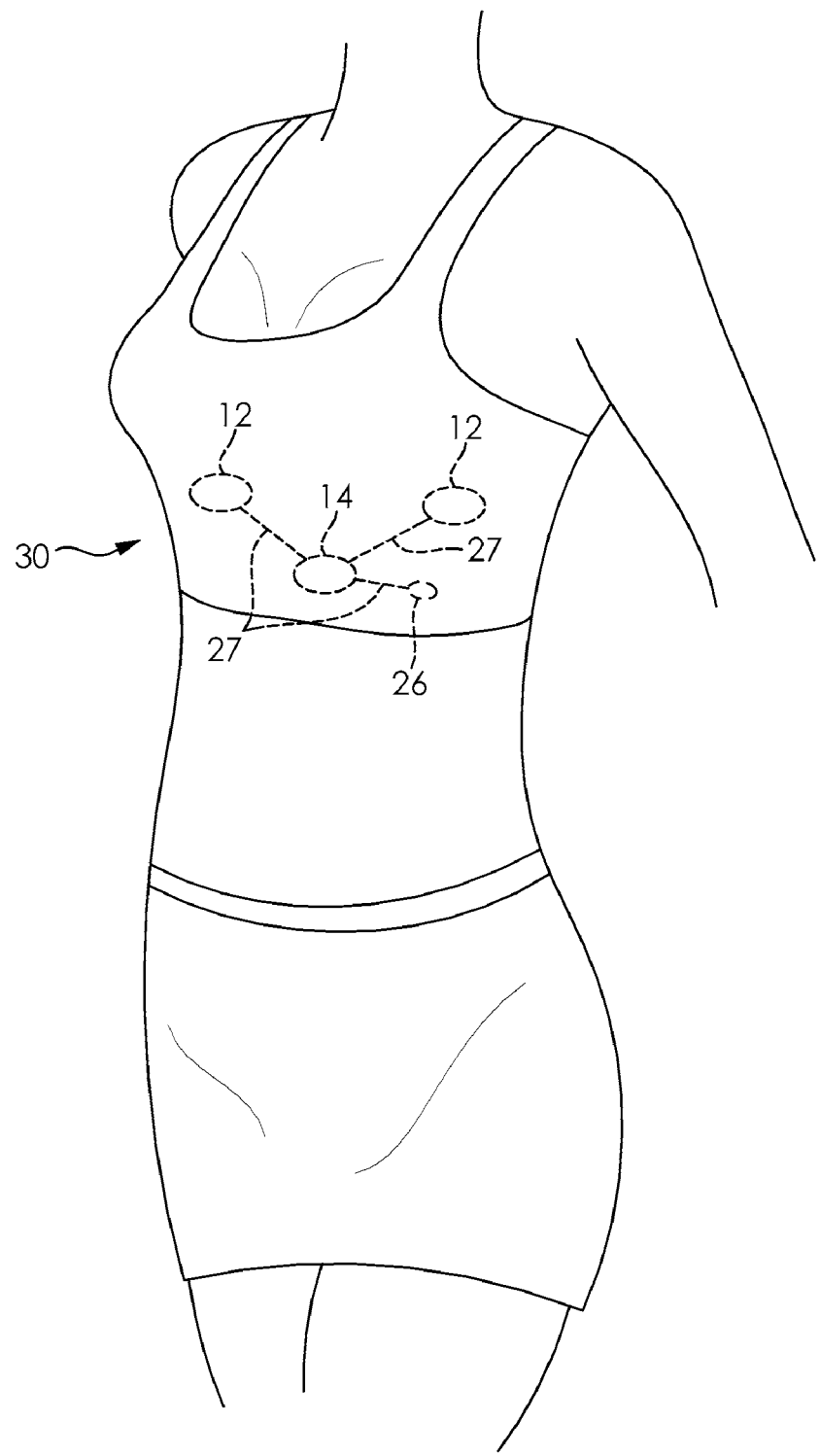
FIG. 4 is a pictorial diagram of a halter-top in accordance with the present invention.
Figure 5:
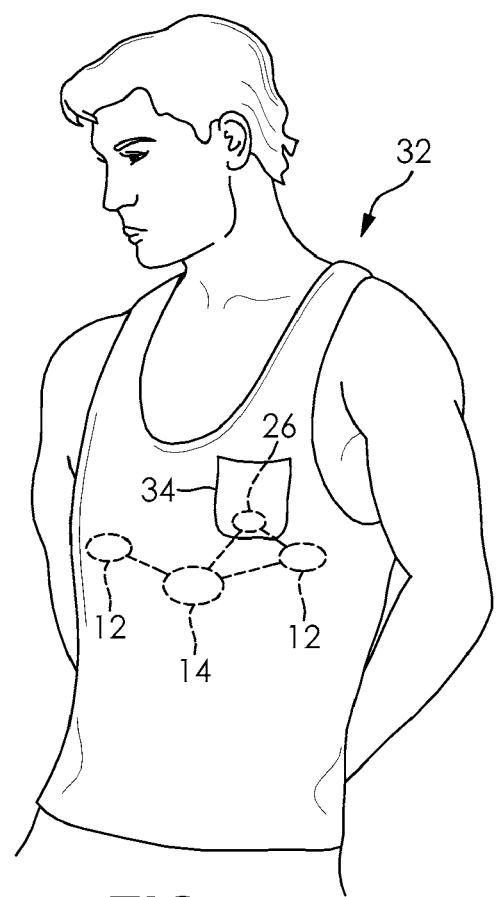
FIG. 5 is a pictorial diagram of a tank top in accordance with the present invention.

FIG. 4 shows a third embodiment of the heart rate monitoring garment 30 accordance with the present invention, in which the power source 26 has been positioned separately from the transmitter 14. The garment 30 is in the form of a halter-top. FIG. 5 is a pictorial diagram of a fourth embodiment of the heart rate monitoring garment 32, in which the power source 26 is preferably located within a pocket 34 of a tank top shirt.

Figure 6:
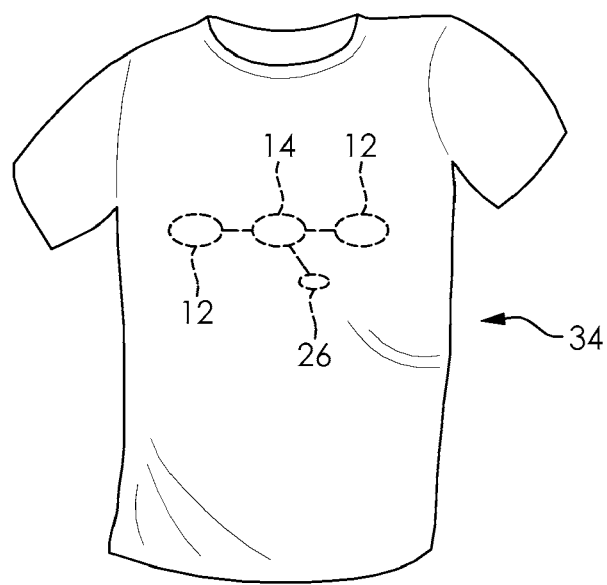
FIG. 6 is a pictorial diagram of a tee shirt in accordance with the present invention.

FIG. 6 is a pictorial diagram of a fifth embodiment of the heart rate monitoring garment 34 accordance with the present invention. The garment 34 is in the form of a tee shirt or athletic shirt, in which the transmitter 14 and electrodes 12 are located substantially collinearly.

Figure 7:
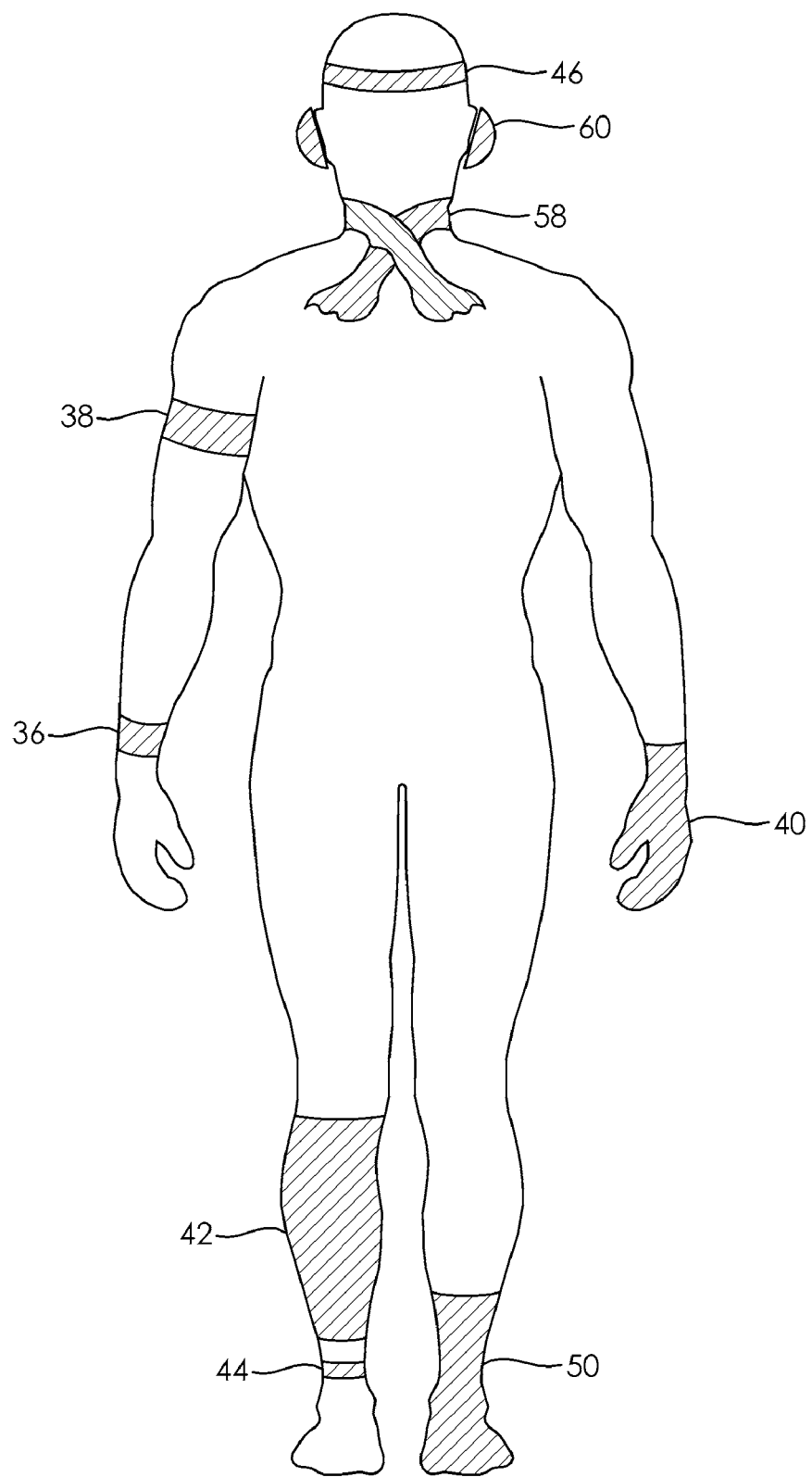
FIG. 7 is a pictorial diagram of a headband, armband, wristband, glove, leg warmer, ankle band, and sock in accordance with the present invention.

FIG. 7 is a pictorial diagram of additional embodiments of the heart rate monitoring garment in accordance with the present invention. The garments shown in FIG. 7 are shown in the form of a wristband 36, armband 38, glove 40, leg warmer 42, ankle band 44, headband 46, sock 50, scarf 58, and earmuffs 60. It is anticipated that the heart rate monitoring garment of the present invention may assume forms and dimensions adapted for placement about various portions of the body while remaining within the scope of the present invention.

The power source 26 may include a rechargeable and/or replaceable battery. In these cases, access to the power source 26, which may be partially or completely removable, is preferably provided by an opening in the garment, or a conductive portion, such as a conductive fiber or patch woven into the garment. Alternatively, the power source 26 may be discarded with the garment upon depletion of its energy reserve without requiring access thereto for recharge or replacement.

Figure 8C:
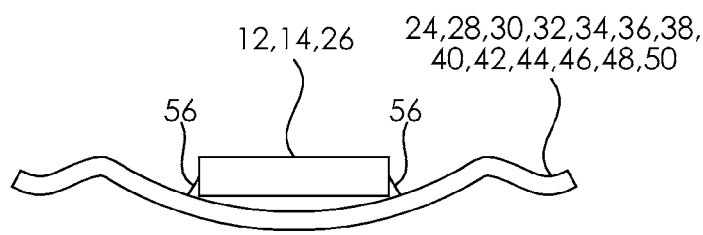
FIGS. 8a, 8b, 8c, 9a, 9b, 9c, 10a, 10b, and 10c are cross-sectional views of the transmitter, power source, and electrodes integrated with the garment in accordance with various embodiments of the present invention.
Figure 8A:
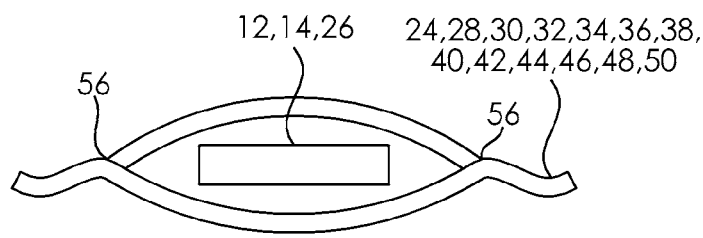
Figure 8B:
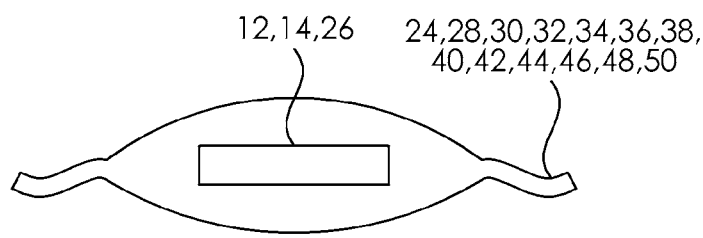

FIGS. 8a and 8b are cross-sectional views of two embodiments concerning integration of the electrodes 12, transmitter 14, and/or power source 26 with the garment 24, 28, 30, 32, 34, 36, 38, 40, 42, 44, 46, 48, and 50. In FIG. 8a, the electrodes 12, transmitter 14, and/or power source 26 are at least partially enclosed within separate layers or plies of the garment 24, 28, 30, 32, 34, 36, 38, 40, 42, 44, 46, 48, and 50, such as in a pocket, pouch, or other enclosure attached by, for example, sewn stitches 56, welding, adhesive, snaps, zippers, hook and loop fastenings, and the like. FIG. 8b shows a second embodiment in which the electrodes 12, transmitter 14, and/or power source 26 are woven into a single layer or ply of the garment 24, 28, 30, 32, 34, 36, 38, 40, 42, 44, 46, 48, and 50.

FIG. 8c, shows another embodiment in which the electrodes 12, transmitter 14, and/or power source 26 are attached to an external or internal face of the garment 24, 28, 30, 32, 34, 36, 38, 40, 42, 44, 46, 48, and 50 by, for example, sewn stitches 56, welding, adhesive, snaps, zippers, hook and loop fastenings, and the like. If required, the electrodes 12, transmitter 14, and/or power source 26 in the embodiments shown in FIGS. 8a, 8b, and 8c, preferably make electrical contact with the user through the garment 24, 28, 30, 32, 34 by means of a conductive medium, such as moisture caused by perspiration.

Figure 9C:
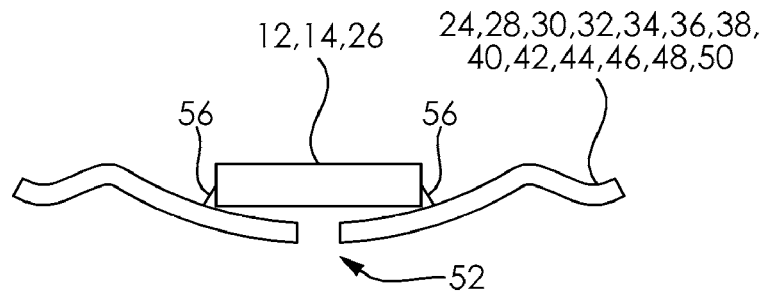
Figure 9A:
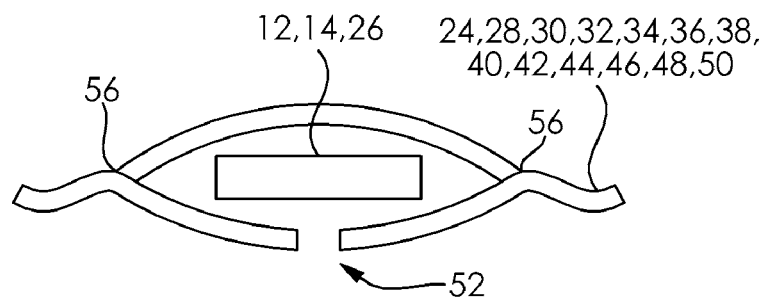
Figure 9B:
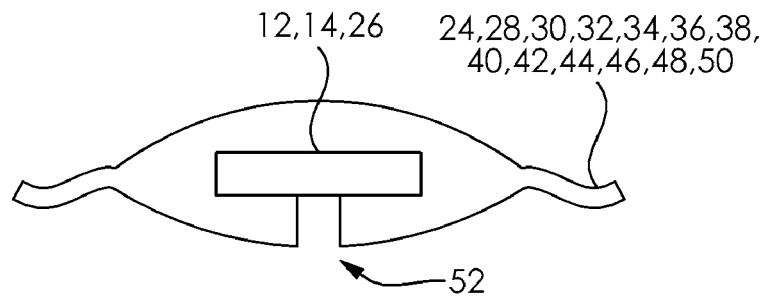

FIGS. 9a and 9b show additional embodiments concerning integration of the electrodes 12, transmitter 14, and/or power source 26 with the garment 24, 28, 30, 32, 34, 36, 38, 40, 42, 44, 46, 48, and 50. FIG. 9c shows another embodiment in which the electrodes 12, transmitter 14, and/or power source 26 are attached to an external or internal face of the garment 24, 28, 30, 32, 34, 36, 38, 40, 42, 44, 46, 48, and 50 by, for example, sewn stitches 56, welding, adhesive, snaps, zippers, hook and loop fastenings, and the like. In these embodiments, if required, an opening is made in the garment to enable contact with the user, such as a circular or oval opening 52, in a separate ply of the garment, as shown in FIG. 9a, or a single ply of the garment, as shown in FIGS. 9b and 9c.

Figure 10C:
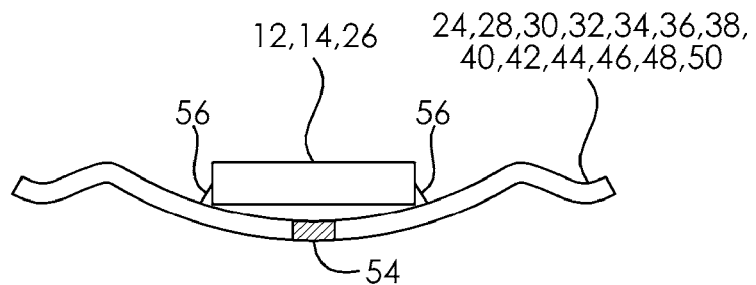
Figure 10A:
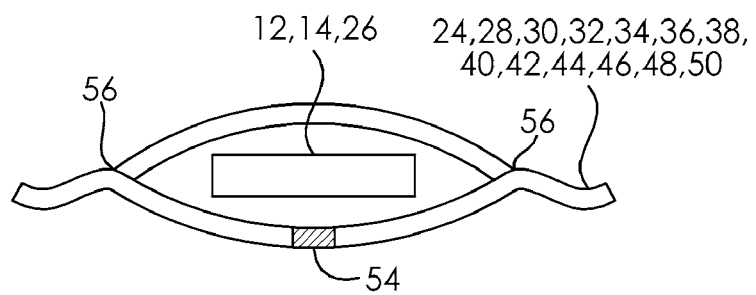
Figure 10B:
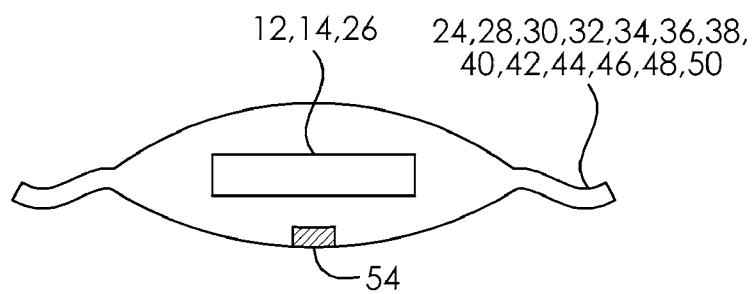

FIGS. 10a and 10b show additional embodiments concerning integration of the electrodes 12, transmitter 14, and/or power source 26 with the garment 24, 28, 30, 32, 34, 36, 38, 40, 42, 44, 46, 48, and 50. FIG. 10c shows another embodiment in which the electrodes 12, transmitter 14, and/or power source 26 are attached to an external or internal face of the garment 24, 28, 30, 32, 34, 36, 38, 40, 42, 44, 46, 48, and 50 by, for example, sewn stitches, welding, adhesive, snaps, zippers, hook and loop fastenings, and the like 56. In these embodiments, if required, the garment incorporates a conductive patch, fiber, and/or material 54 between the electrodes 12, transmitter 14, and/or power source 26 and the user in the multi-ply embodiment shown in FIG. 10a, and the single ply embodiments shown in FIGS. 10b and 10c.

The garments 24, 28, 30, 32, 34, 36, 38, 40, 42, 44, 46, 48, and 50, which include the transmitter 14, electrodes 12, and power source 26, are preferably worn, washed, and discarded as an integral unit. The transmitter 14, electrodes 12, and power source 26 preferably cannot be removed from the garment without fracturing the garment. Placement of the transmitter 14, electrodes 12, and power source 26 is preferably such that these components are not too obtrusive, do not affect comfort, and will not interfere with normal use, washing in accordance with the manufacturer's instructions, and disposal of the garments 24, 28, 30, 32, 34, 36, 38, 40, 42, 44, 46, 48, and 50, while retaining these components substantially in place by limiting their movement with respect to the garment.

In order to conserve energy, the transmitter 14 is preferably activated and transmits signals to the receiver in response to being worn, such as by detecting pressure or moisture, or selection of an externally accessible switch. Washing is preferably done in accordance with the manufacturer's instructions by hand or machine.

The invention thus provides an effective and reliable method and apparatus that integrate a transmitter, power source, and electrodes of a heart rate monitor with a garment. The invention further provides a garment having an embedded heart rate transmitter, power source, and electrodes that can be worn, washed, and discarded as an integral unit.

The subject invention also provides a method and apparatus for reducing the quantity of equipment required during an exercise session. The invention further provides a method and apparatus for making a heart rate monitor less restrictive, obtrusive, or likely to slip and more comfortable to wear.

Although the illustrative embodiments of the present invention have been described herein with reference to the accompanying drawings, it is to be understood that the invention is not limited to those precise embodiments and that various other changes and modifications may be effected therein by one skilled in the art without departing from the scope or spirit of the invention

What is claimed is:

1. A garment to monitor a user's heart rate, the garment comprising:
    material;
    a wireless transmitter, the wireless transmitter being integrated with the material and providing and transmitting information representing the user's heart rate;
    an electrode, the electrode being operatively coupled to the wireless transmitter and integrated with the material, the electrode being responsive to the user's heart rate by detecting the user's electrocardiogram;
    an electrically conductive portion disposed between the electrode and the user; and
        a power source, the power source being operatively coupled to the wireless transmitter and integrated with the material, the garment being configured to be worn with the electrode, transmitter, and power source integrated therewith, and wherein the wireless transmitter, electrode and power source are inseparable from the garment without fracturing the garment by removing stitching or welding.

2. The garment defined by claim 1, wherein the material is configured to be worn as at least one of a brassiere, sports brassiere, halter-top, tank top shirt, tee shirt, wristband, headband, armband, ankle band, leg warmer, scarf, earmuffs, sock, and glove.

3. The garment defined by claim 1, wherein the power source comprises a battery.

4. The garment defined by claim 3, wherein the battery is at least one of rechargeable and replaceable.

5. The garment defined by claim 1, wherein at least one of the electrode, wireless transmitter, and power source is at least partially embedded within a plurality of layers of the material.

6. The garment defined by claim 1, wherein at least one of the electrode, wireless transmitter, and power source is at least partially embedded within a layer of the material.

7. The garment defined by claim 1, wherein the electrically conductive portion comprises at least one of a conductive fiber, conductive material, and conductive fluid.

8. The garment defined by claim 1, wherein the wireless transmitter at least one of transmits information representing the user's heart rate and stores information representing the user's heart rate.

9. The garment defined by claim 1, wherein the garment is configured to be washed with the electrode, wireless transmitter, and power source integrated therewith and discarded with the electrode, wireless transmitter, and power source integrated therewith.

10. A garment to monitor a user's heart rate, the garment comprising:
    material;
    a wireless transmitter, the wireless transmitter being at least partially embedded in the material and providing and transmitting information representing the user's heart rate;
    an electrode, the electrode being operatively coupled to the wireless transmitter, the electrode being at least partially embedded in the material, the electrode being responsive to the user's heart rate by detecting the user's electrocardiogram;
    an electrically conductive portion disposed between the electrode and the user; and
    a power source, the power source being operatively coupled to the wireless transmitter, the power source being at least partially embedded in the material, the garment being adapted for being worn with the electrode, wireless transmitter, and power source at least partially embedded therein, and wherein the wireless transmitter, electrode and power source inseparable from the garment without fracturing the garment by removing stitching or welding.

11. The garment defined by claim 10, wherein the material is configured to be worn as at least one of a brassiere, sports brassiere, halter-top, tank top shirt, tee shirt, wristband, headband, armband, ankle band, leg warmer, scarf, earmuffs, sock, and glove.

12. The garment defined by claim 10, wherein the power source comprises a battery.

13. The garment defined by claim 12, wherein the battery is at least one of rechargeable and replaceable.

14. The garment defined by claim 10, wherein at least one of the electrode, wireless transmitter, and power source is at least partially embedded within a plurality of layers of the material.

15. The garment defined by claim 10, wherein at least one of the electrode, wireless transmitter, and power source is at least partially embedded within a layer of the material.

16. The garment defined by claim 10, wherein the electrically conductive portion comprises at least one of a conductive fiber, conductive material, and conductive fluid.

17. The garment defined by claim 10, wherein the wireless transmitter at least one of transmits information representing the user's heart rate and stores information representing the user's heart rate.

18. The garment defined by claim 10, wherein the garment is configured to be washed with the electrode, wireless transmitter, and power source at least partially embedded therein.

19. A method of monitoring a user's heart rate comprising:
    integrating a wireless transmitter, electrode, and power source with a garment, wherein the wireless transmitter, electrode and power source are inseparable from the garment without fracturing the garment by removing stitching or welding;
    coupling the electrode operatively to the wireless transmitter, the electrode being responsive to the heart rate by detecting the user's electrocardiogram, the wireless transmitter being adapted for providing and transmitting information representing the user's heart rate;
    disposing an electrically conductive portion between the electrode and the user; and
    coupling the power source operatively to the wireless transmitter the garment configured to be worn and washed with the wireless transmitter, electrode, and power source integrated therewith.

20. A garment to monitor a user's heart rate, the garment comprising:
    material;
    a wireless transmitter, the wireless transmitter being at least partially embedded within within at least one layer of the material and providing and transmitting information representing the user's heart rate;
    an electrode, the electrode being operatively coupled to the wireless transmitter, the electrode being at least partially embedded within a plurality of layers or within a layer of the material, the electrode being responsive to the user's heart rate by detecting the user's electrocardiogram;

an electrically conductive portion disposed between the electrode and the user; and a power source, the power source being operatively coupled to the wireless transmitter, the power source being at least partially embedded in the material, the garment being adapted for configured to be worn with the electrode, wireless transmitter, and power source at least partially embedded therein.

21. A method of monitoring a user's heart rate comprising:

integrating a wireless transmitter, electrode, and power source with a garment;

embedding the electrode and wireless transmitter at least partially within at least one layer of the garment;

coupling the electrode operatively to the wireless transmitter, the electrode being responsive to the heart rate by detecting the user's electrocardiogram, the wireless transmitter being adapted for providing and transmitting information representing the user's heart rate;

disposing an electrically conductive portion between the electrode and the user; and coupling the power source operatively to the wireless transmitter, the garment configured to be worn and washed with the wireless transmitter, electrode, and power source integrated therewith.

* * * * *